United States Patent
Amao et al.

(10) Patent No.: US 9,777,299 B2
(45) Date of Patent: Oct. 3, 2017

(54) OXIDOREDUCTASE REACTION CONTROL AND USE THEREOF

(71) Applicant: Amano Enzyme Inc., Nagoya-shi (JP)

(72) Inventors: Yutaka Amao, Osaka (JP); Shusaku Ikeyama, Osaka (JP); Yuji Nakanishi, Kakamigahara (JP); Tetsuya Takahashi, Kakamigahara (JP); Satoshi Koikeda, Kakamigahara (JP)

(73) Assignee: AMANO ENZYME INC., Nagoya-Shi (JP)

( * ) Notice: Subject to any disclaimer, the term of this patent is extended or adjusted under 35 U.S.C. 154(b) by 0 days.

(21) Appl. No.: 14/408,127

(22) PCT Filed: Jun. 13, 2013

(86) PCT No.: PCT/JP2013/066383
§ 371 (c)(1),
(2) Date: Dec. 15, 2014

(87) PCT Pub. No.: WO2013/187485
PCT Pub. Date: Dec. 19, 2013

(65) Prior Publication Data
US 2015/0176037 A1    Jun. 25, 2015

(30) Foreign Application Priority Data

Jun. 16, 2012 (JP) .................................. 2012-136452
Jun. 21, 2012 (JP) .................................. 2012-139887

(51) Int. Cl.
*C12P 7/40* (2006.01)
*C12P 7/04* (2006.01)
(Continued)

(52) U.S. Cl.
CPC .............. *C12P 7/40* (2013.01); *C12M 21/18* (2013.01); *C12N 9/0004* (2013.01); *C12N 11/14* (2013.01);
(Continued)

(58) Field of Classification Search
CPC ...... C12P 7/40; C12P 3/00; C12P 7/04; C12P 7/24; C12M 21/18; C12N 11/14; C12N 9/0004
See application file for complete search history.

(56) References Cited

FOREIGN PATENT DOCUMENTS

| JP | 2006-508519 A | 3/2006 |
|----|---------------|--------|
| JP | 2010-063453 A | 3/2010 |

(Continued)

OTHER PUBLICATIONS

Kodaka et al. J. Chem. Soc. Perkin Tans. 2 (1999) 891-894.*
(Continued)

*Primary Examiner* — Alexander Kim
(74) *Attorney, Agent, or Firm* — Locke Lord, LLP; James Armstrong, IV; Nicholas R. Herrel

(57) ABSTRACT

The present invention is intended to prove a technique useful for controlling the reaction of oxidoreductase, and to provide a reaction system allowing efficient conversion from carbon dioxide to formic acid, and an efficient methanol production system including the reaction system. The reverse redox reaction is selectively promoted by carrying out the reaction catalyzed by an oxidoreductase using an artificial electron carrier. The reaction system is used for the production of methanol.

9 Claims, 18 Drawing Sheets

(51) Int. Cl.
    C12P 7/24      (2006.01)
    C12P 3/00      (2006.01)
    C12N 9/02      (2006.01)
    C12N 11/14     (2006.01)
    C12M 1/40      (2006.01)

(52) U.S. Cl.
    CPC      *C12P 3/00* (2013.01); *C12P 7/04* (2013.01); *C12P 7/24* (2013.01)

(56) References Cited

FOREIGN PATENT DOCUMENTS

WO    WO-2004/051774 A2    6/2004
WO    WO-2006/057387 A1    6/2006

OTHER PUBLICATIONS

Supplementary European Search Report dated Dec. 15, 2015, issued for the European patent application No. 13803471.5.
Y. Amao et al., "Development of artificial leaf for solar hydrogen production", Energy Procedia, vol. 29, 2012, pp. 21-25.
Amao, "Carbon dioxide fixation based on the artificial photosynthesis system", The 90th Annual Meeting of CSJ, 2011, Yokohama, Japan Conference paper, 2011, p. 1, XP002751662.
I. Tsujisho et al., "Photochemical and enzymatic synthesis of formic acid from $CO_2$ with chlorophyll and dehydrogenase system", Catalysis Communications, vol. 7, 2006, pp. 173-176.
R. Miyatani et al., "Bio-$CO_2$ fixation with formate dehydrogenase from *Saccharomyces cerevisiae* and water-soluble zinc porphyrin by visible light", Biotechnology Letters, vol. 24, 2002, pp. 1931-1934.
S. Fukuzumi et al., "Catalytic mechanisms of hydrogen evolution with homogeneous and heterogeneous catalysts", Energy & Environmental Science, vol. 4, 2011, pp. 2754-2766.
S. Ikeyama et al., "Development of an artificial co-enzyme for formate dehydrogenase with the function of CO2 reduction", Honolulu PRIME 2012, Oct. 2012 Conference paper, Oct. 2012, 1 page, XP002751686.
Yutaka Amao et al., "Photochemical and Enzymatic Synthesis of Methanol from $HCO_3^-$ with Dehydrogenases and Zinc Porphyrin", Chemistry Letters vol. 33, No. 12, 2004, pp. 1544-1545.
Daniel Mandler et al., "Photochemical Fixation of Carbon Dioxide: Enzymic Photosynthesis of Malic, Aspartic, Isocitric, and Formic Acids in Artificial Media", J. Chem. Soc., Perkin Trans., II, 1988, pp. 997-1003.
Yutaka Amao, "Solar Fuel Production Based on the Artificial Photosynthesis System", ChemCatChem, 2011, vol. 3 No. 3, pp. 458-474.
Amao, Y. et al., "Photochemical and Enzymatic Methanol Synthesis from $HCO_3^-$ by Dehydrogenases Using Water-soluble Zinc Porphyrin in Aqueous Media", Appl. Catal. B: Environmental, 2009, vol. 86 No. 3-4, pp. 109-113.
Amao, Y. et al., "Highly efficient photochemical hydrogen production system using zinc porphyrin and hydrogenase in CTAB micellar system", Solar Energy Materials & Solar Cells, 2003, vol. 79 No. 1, pp. 103-111.
Amao, Y. et al., "Artificial Leaf Device for Solar Fuel Production", Faraday Discuss., vol. 155, 2012, pp. 289-296.
International Search Report mailed Sep. 17, 2013, issued for PCT/JP2013/066383.
Japanese Office Action issued Mar. 21, 2017, JP Patent Application 2014-521409.
Yutaka Amao, Chemical Engineering vol. 57, No. 3, 186-191 (2012)—Figure 6.
Yutaka Amao, Device Application of Photosynthetic Pigment-Protein Complex, Bio Industry, vol. 29, No. 1 (2012), 34-41—Figure 9.

* cited by examiner

[Fig. 1]
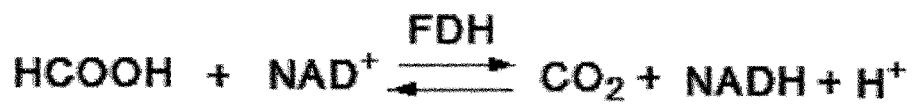
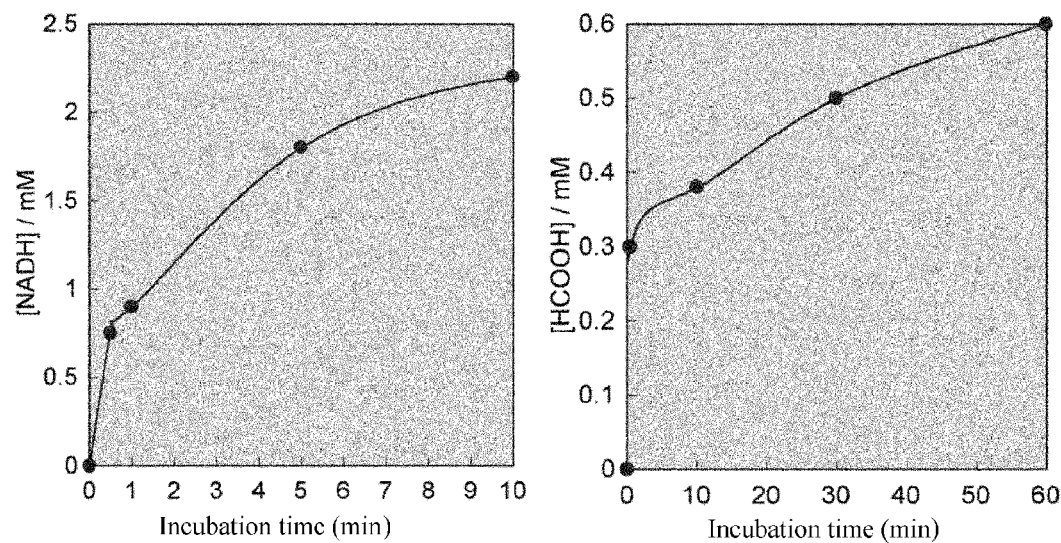

[Fig. 2]
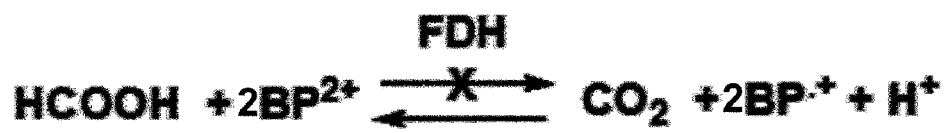
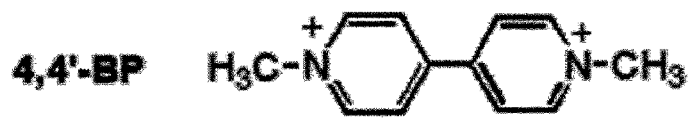
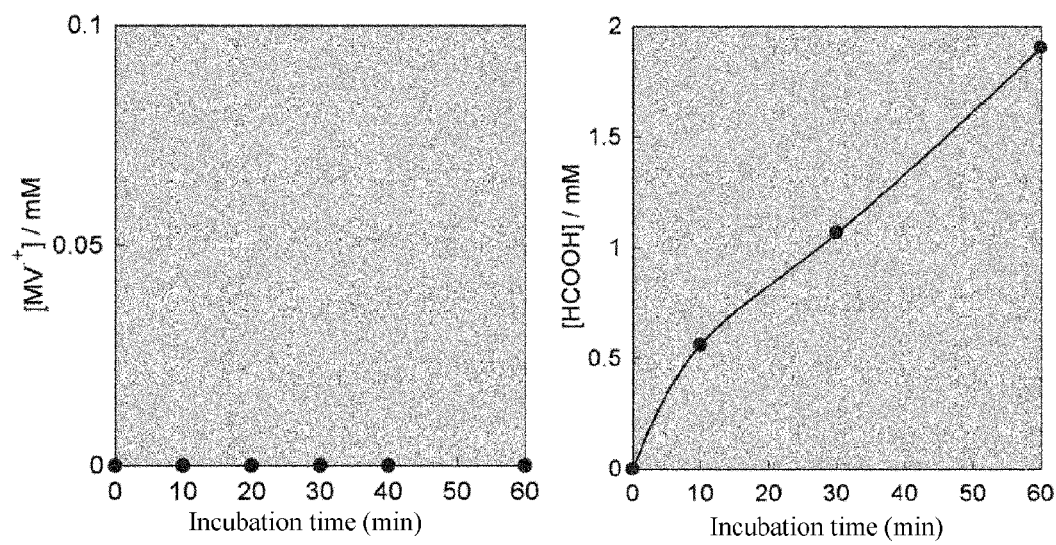

[Fig. 3]
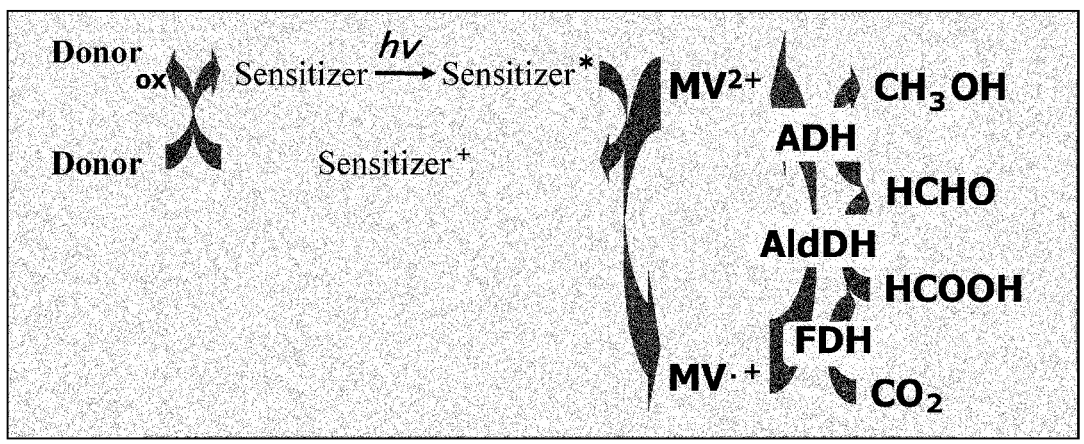

[Fig. 4]
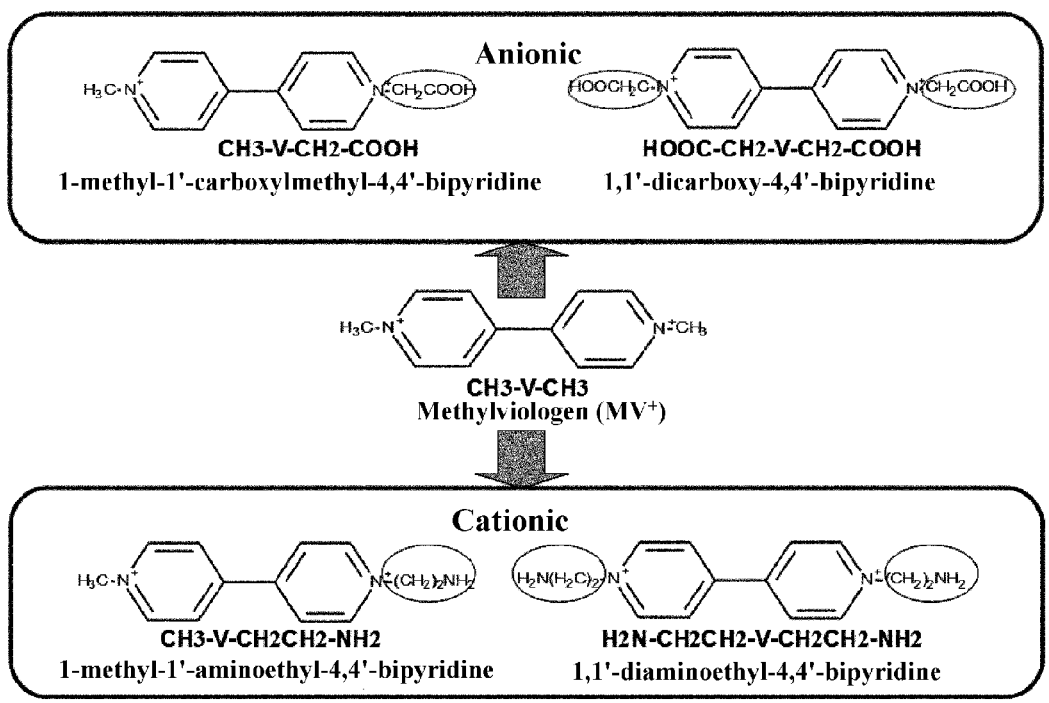

[Fig. 5]
A 
B 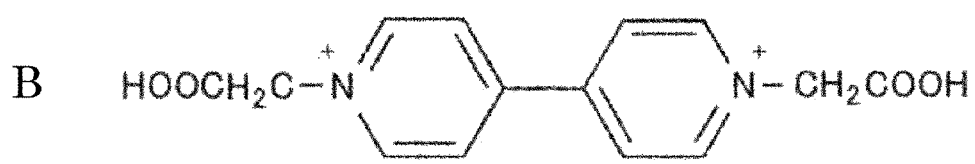
C 
D 
$MV^{2+}$ 

[Fig. 6]
- Measurement of reduction potential by cyclic voltammetry (CV)
  | Working electrode: C electrode |
  | Reference electrode: Ag/AgCl electrode |
  | Counter electrode: Pt electrode |
- Comparison of the reaction rate of formic acid by the difference of structure of artificial coenzymes
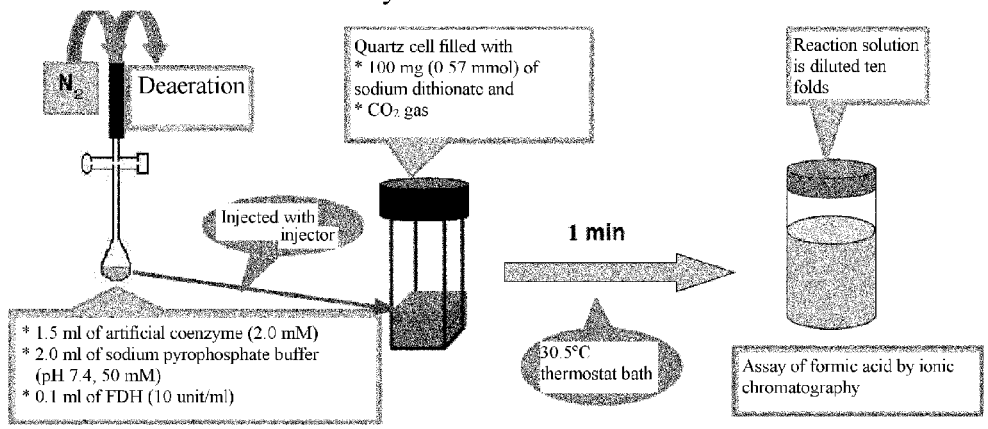

[Fig. 7]

Structure of artificial coenzyme and reduction potential

| Structure of artificial coenzyme | Reduction potential (V) |
|---|---|
| A $CH_3$-V-$CH_2$-COOH | −0.67 |
| B HOOC-$CH_2$-V-$CH_2$-COOH | −0.67 |
| C $CH_3$-V-$(CH_2)_2$-$NH_2$ | −0.62 |
| D $H_2N$-$(CH_2)_2$-V-$(CH_2)_2$-$NH_2$ | −0.60 |
| $MV^{2+}$ | −0.67 |

[Fig. 8]

Structure formula of artificial coenzyme and formation of formic acid

| Structure of artificial coenzyme | Formation of formic acid ($\mu$M) |
|---|---|
| A $CH_3$-V-$CH_2$-COOH | 52.6 |
| B HOOC-$CH_2$-V-$CH_2$-COOH | 30.8 |
| C $CH_3$-V-$(CH_2)_2$-$NH_2$ | 84.2 |
| D $H_2N$-$(CH_2)_2$-V-$(CH_2)_2$-$NH_2$ | 102.8 |
| $MV^{2+}$ | 69.9 |

[Fig. 9]

| Structure of artificial coenzyme | Positive charge | Reduction potential(V) | Formation of formic acid (μM) |
|---|---|---|---|
| D $H_2N-(CH_2)_2-V-(CH_2)_2-NH_2$ | +4 | −0.60 | 102.8 |
| C $CH_3-V-(CH_2)_2-NH_2$ | +3 | −0.62 | 84.2 |
| $MV^{2+}$ | +2 | −0.67 | 69.9 |
| A $CH_3-V-CH_2-COOH$ | +1 | −0.67 | 52.6 |
| B $HOOC-CH_2-V-CH_2-COOH$ | 0 | −0.67 | 30.8 |

[Fig. 10]
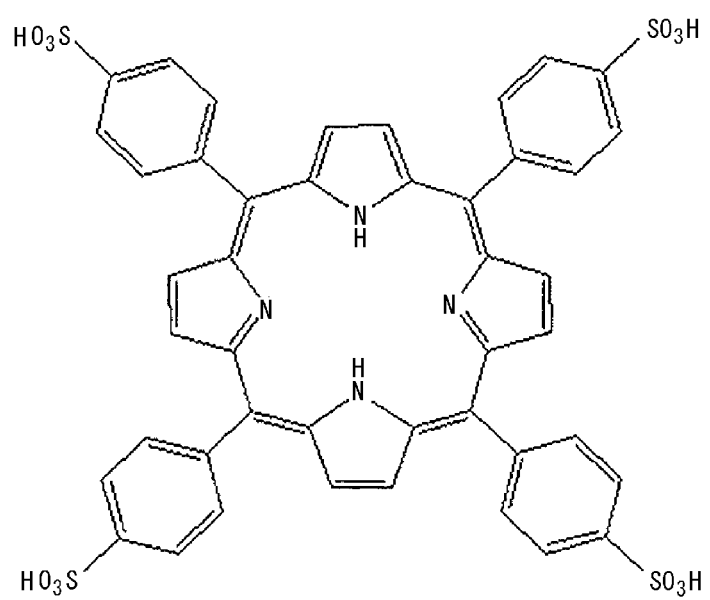

[Fig. 11]
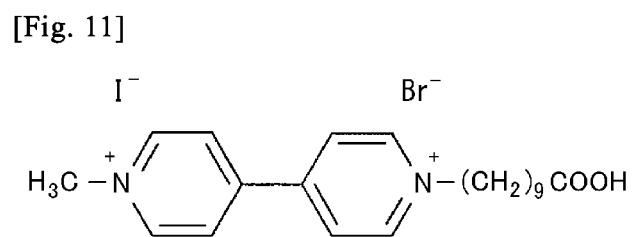

[Fig. 12]
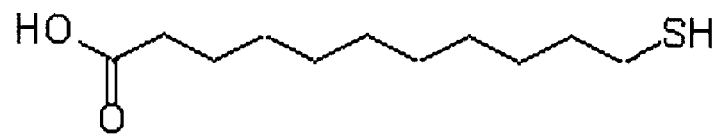

[Fig. 13]
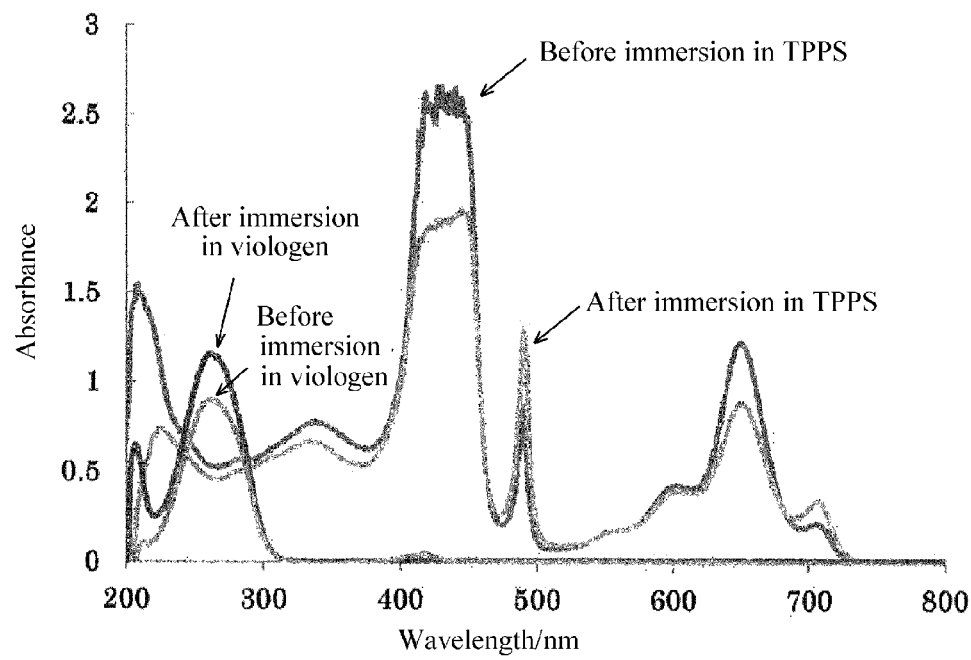

[Fig. 14]

|  | Amount of adsorption (nmol/cm$^2$) | Percentage of adsorption (%) |
|---|---|---|
| TPPS | 0.36 | 20.8 |
| Viologen | 0.4 | 22.5 |

[Fig. 15]
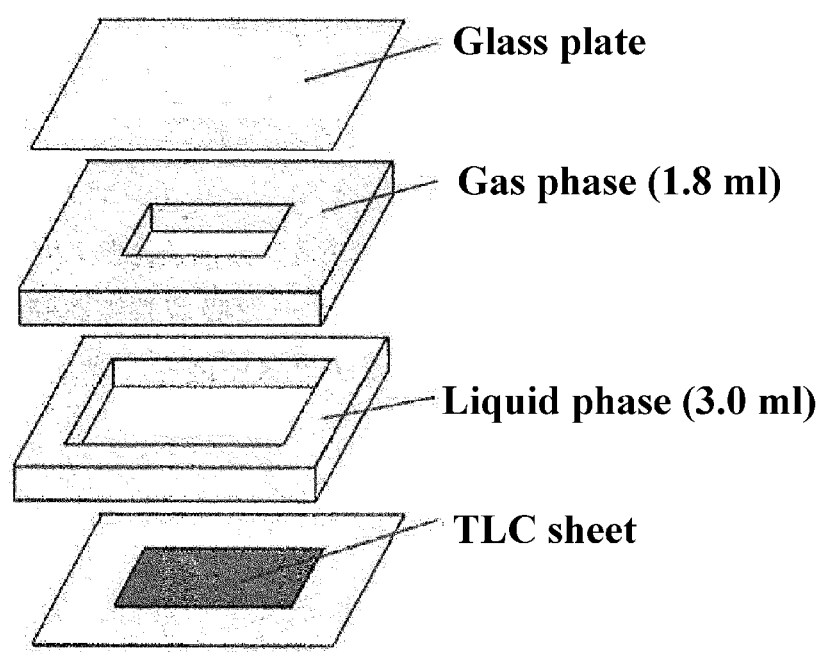

[Fig. 16]
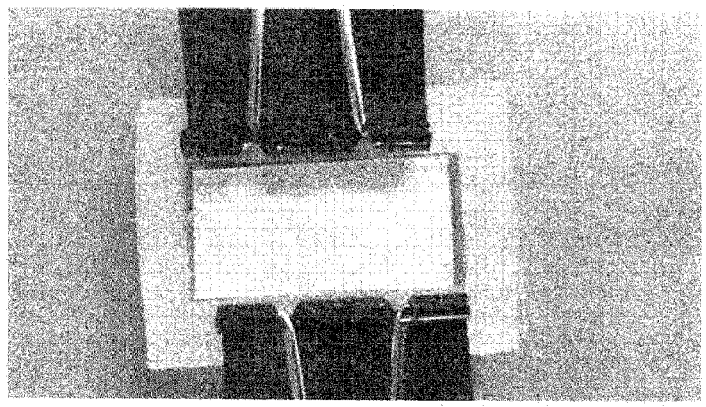
Before irradiation with visible light
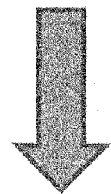
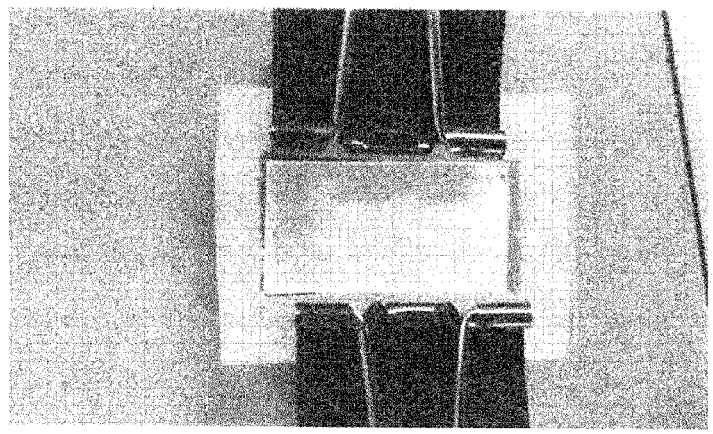
One hour after irradiation with visible light

[Fig. 17]
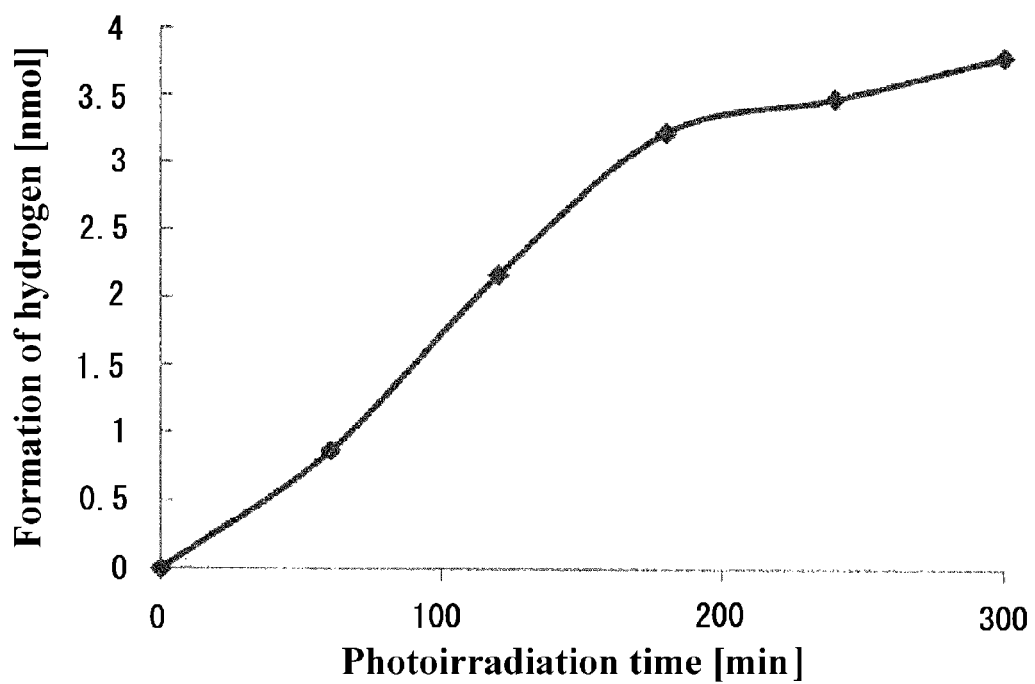

[Fig. 18]
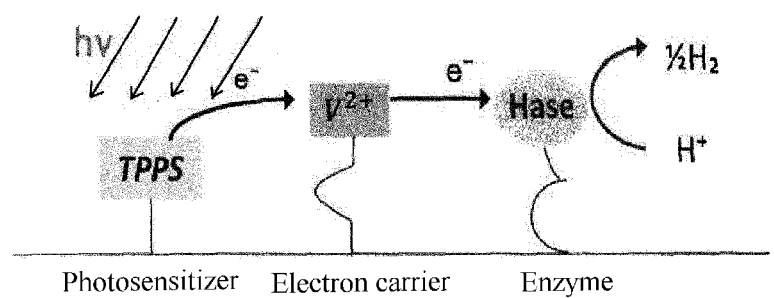

OXIDOREDUCTASE REACTION CONTROL AND USE THEREOF

TECHNICAL FIELD

The present invention relates to the improvement and the use of a reaction system catalyzed by an oxidoreductase, and specifically to a method for selectively promoting reverse redox reaction using a specific electron carrier, and the method for producing methanol using the promotion method. The present application claims priority based on Japanese Patent Application No. 2012-136452 filed on Jun. 16, 2012 and Japanese Patent Application No. 2012-139887 filed on Jun. 21, 2012, and the content of the patent applications is hereby incorporated by reference herein in its entirety.

BACKGROUND ART

Oxidoreductases play important roles in living bodies, such as involvement in metabolism and energy production. In addition, oxidoreductases are extremely useful for industries, and are used for the measurement and calibration for the purposes of analysis and diagnosis. In recent years, oxidoreductases are used also in the field of bioenergy. For example, Patent Literatures 1 and 2 show the use of dehydrogenase formate, aldehyde dehydrogenase, and alcohol dehydrogenase in fuel cells operated with methanol.

CITATION LIST

Patent Literature

[Patent Literature 1] WO 2006/057387
[Patent Literature 2] Japanese Unexamined Patent Application Publication No. 2006-508519

Non-Patent Literature

[Non-Patent Literature 1] Chemistry Letters Vol. 33, No. 12, 1544-1545
[Non-Patent Literature 2] D. Mandler, I. Willner, *J. Chem. Soc., Perkin Trans.*, 2, 997 (1988).

SUMMARY OF INVENTION

Technical Problem

Oxidoreductase reaction is generally reversible. Therefore, it is very important for the use of oxidoreductase to control the reaction, more specifically to selectively and efficiently promote only the necessary reaction, namely the forward reaction or the reverse one. For example, the reaction can be controlled by the modification of the enzyme by protein engineering and adjustment of the reaction conditions (for example, adjustment of the loading of the substrate and the abundance of the reaction product, or the adjustment of the temperature conditions). However, there are some oxidoreductases to which such prior art methods are not sufficiently effective. For example, in the optically driven carbon dioxide-methanol conversion system (Non-Patent Literature 1) reported by the study group of the inventors, reduction reactions by three dehydrogenases (formate dehydrogenase (FDH), aldehyde dehydrogenase (AldDH), and alcohol dehydrogenase (ADH)) are continuously promoted, whereby carbon dioxide is converted into formic acid, formic acid into formaldehyde, and formaldehyde into methanol, successively. The first stage reaction (the reaction converting carbon dioxide into formic acid), which is most important for increasing efficiency of the reaction system, is a reverse reaction by formate dehydrogenase, so that its selectivity is difficult to be increased.

In view of the above-described circumstances, the present invention is intended to provide a technique useful for the control of oxidoreductase reaction. In addition, as an application of the technique, the present invention is also intended to provide a reaction system which allows efficient conversion from carbon dioxide into formic acid, and an efficient methanol production system including this system.

Solution to Problem

In order to solve the above-described problems, the inventors focused on the study of the reaction system of formate dehydrogenase, from a new viewpoint of using artificial coenzymes (electron carriers, mediators) in place of natural coenzymes (for example, $NAD^+$). Non-Patent Literature 2 reports a reaction system of a formate dehydrogenase using methylviologen as an artificial coenzyme. However, there are many obscure points, such as the degree of progress of reverse reaction, or whether the reverse reaction can be selectively promoted or not. Accordingly, characteristics of the formate dehydrogenase reaction system using methylviologen as an artificial coenzyme were studied in detail. As a result of this, surprisingly, it was revealed that the forward reaction does not substantially proceed when methylviologen is used, and reverse reaction markedly selectively proceeds. After obtaining this finding, with the aim of further increasing the efficiency of the reaction, artificial coenzymes composed of 4,4'-bipyridine (BP) and various ionic substituents were synthesized, and their usefulness was compared. As a result of detailed study, important and attractive findings were obtained for the relationship between the chemical structure of the artificial coenzymes and enzymatic activity.

On the basis of the above studies, it was revealed that the use of artificial coenzymes is effective for the control of the reaction of oxidoreductases, and artificial coenzymes which effective for efficient reaction were found. In order to orient the oxidoreductase reaction to one direction, at present, complicated and not so effective means, such as the modification of the enzyme itself using protein engineering, and adjustment of reaction conditions must be used. Under such circumstances, the above-described findings revealed by the inventors include the improvement of coenzymes (mediators), and provide a resolution means which is expected to increase the efficiency in a novel and dramatic manner. They have marked meaning, and are expected to be used in a wide range of fields as a new means for modifying enzymatic reaction. The present invention shown below is mainly based on these findings.

[1] A method for selectively promoting a reverse redox reaction, including carrying out the reaction catalyzed by an oxidoreductase using an artificial electron carrier.

[2] A method for selectively promoting reverse redox reaction, including carrying out the reaction catalyzed by an oxidoreductase using a viologen compound or a bipyridinium salt derivative as an electron carrier.

[3] The method of [1] or [2], wherein the oxidoreductase is an NAD-dependent enzyme.

[4] The method of [3], wherein the NAD-dependent enzyme is an enzyme selected from the group consisting of formate dehydrogenase, aldehyde dehydrogenase, alcohol dehydrogenase, lactate dehydrogenase, and glutamate dehydrogenase.

[5] The method of any one of [1] to [4], wherein the electron carrier is the compound of any one of the formulae (1) to (9):

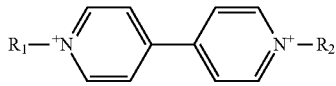

wherein R1 and R2 are each independently a substituted or unsubstituted alkyl group, a substituted or unsubstituted aryl group, or a substituted or unsubstituted arylalkyl group, and the substituted or unsubstituted alkyl group has 1 to 12 carbon atoms, the substituted or unsubstituted aryl group has 6 to 20 carbon atoms, and the substituted or unsubstituted arylalkyl group has 7 to 20 carbon atoms;

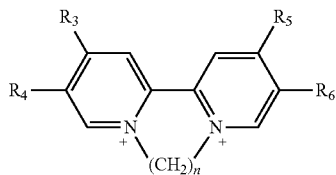

wherein R3, R4, R5, and R6 are each independently a substituted or unsubstituted alkyl group, a substituted or unsubstituted aryl group, or a substituted or unsubstituted arylalkyl group, the substituted or unsubstituted alkyl group has 1 to 12 carbon atoms, the substituted or unsubstituted aryl group has 6 to 20 carbon atoms, and the substituted or unsubstituted arylalkyl group has 7 to 20 carbon atoms;

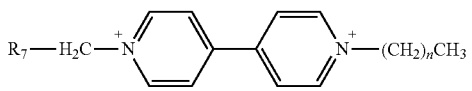

wherein n is an integer of 0 to 10, R7 is a hydrogen atom, a methyl group, a substituted or unsubstituted amino group, a carboxyl group, a t-butyl group, or a benzyl group;

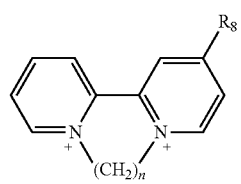

wherein n is an integer of 1 to 10, R8 is a methyl group, a substituted or unsubstituted amino group, a carboxyl group, a t-butyl group, or a benzyl group;

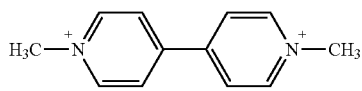

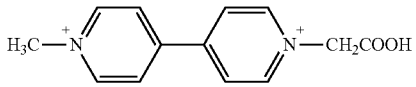

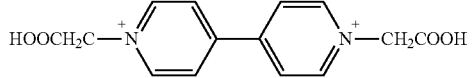

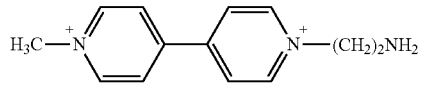

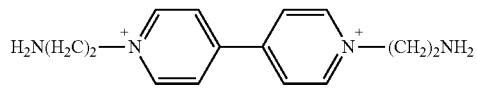

[6] The method of any one of [1] to [5], including the following steps (1) and (2):

(1) a step of reducing the electron carrier to form a reduced electron carrier;

(2) a step of allowing the oxidoreductase to act on the substrate of the reverse reaction in the presence of the reduced electron carrier thus formed.

[7] The method of [6], wherein the step (1) includes a step of allowing a reducing agent to act on the electron carrier, or a step of applying light under the coexistence of the electron carrier, an electron donor, and a photosensitizer.

[8] A method of converting carbon dioxide into formic acid, including carrying out the enzymatic reaction catalyzed by formate dehydrogenase using a viologen compound or a bipyridinium salt derivative as an electron carrier in the presence of carbon dioxide.

[9] The method of [8], including a step of forming the conditions where formate dehydrogenase, the reduced electron carrier, and carbon dioxide coexist in a solution, and allowing the formate dehydrogenase to act on carbon dioxide.

[10] The method of [9], wherein the reduced electron carrier is formed by allowing a reducing agent to act on the electron carrier, or applying light under the coexistence of the electron carrier, electron donor, and photo sensitizer.

[11] The method of any one of [8] to [10], including using the compound defined in [5] as an electron carrier.

[12] A method of producing methanol from carbon dioxide, including the following steps (i) and (ii):

(i) a step of allowing aldehyde dehydrogenase to act on the formic acid, which has formed by the method of any one of [8] to [11], using a viologen compound or a bipyridinium salt derivative as an electron carrier, thereby converting formic acid into formaldehyde;

(ii) a step of converting formaldehyde into methanol by allowing an alcohol dehydrogenase to act on the formaldehyde formed by the step (i) using a viologen compound or a bipyridinium salt derivative as an electron carrier.

[13] The method of [12], including using the compound defined in [5] as the electron carrier in the step (i) and the electron carrier in the step (ii).

[14] A method of producing methanol from carbon dioxide, including the following steps (1) and (2):

(1) a step of forming the conditions where formate dehydrogenase, aldehyde dehydrogenase, alcohol dehydrogenase, a viologen compound or a bipyridinium salt derivative, an electron donor, a photosensitizer, and carbon dioxide coexist in a solution, and (2) applying light to the solution.

[15] The method of [14], wherein the step (1) is composed of the following steps (1-1) and (1-2), or (1-3) to (1-5):

(1-1) a step of adding formate dehydrogenase, aldehyde dehydrogenase, alcohol dehydrogenase, a viologen compound or a bipyridinium salt derivative, an electron donor, and a photosensitizer to the solvent;

(1-2) a step of feeding carbon dioxide to the solution obtained in the step (1-1);

(1-3) a step of adding aldehyde dehydrogenase, alcohol dehydrogenase, a viologen compound or a bipyridinium salt derivative, an electron donor, and a photosensitizer to a solvent;

(1-4) a step of feeding carbon dioxide to the solution obtained in the step (1-3); and (1-5) a step of adding formate dehydrogenase to the solution after (1-4).

[16] A hydrogen production reaction unit including an insoluble support, and a hydrogenase, an artificial electron carrier, and a photosensitizer which are immobilized on the insoluble support.

[17] The hydrogen production reaction unit of [16], wherein the insoluble support is an insoluble support selected from the group consisting of a resin, a metal, a semiconductor, ceramic, and glass.

[18] The hydrogen production reaction unit of [16] or [17], wherein the photosensitizer is selected from the group consisting of a porphyrin derivative, a ruthenium bipyridine complex derivative, a pyrene derivative, and a chlorophyll derivative.

[19] The hydrogen production reaction unit of [16] or [17], wherein the photosensitizer is selected from the group consisting of zinc tetrakis(4-methylpyridyl) porphyrin (ZnTMPyP), tetraphenyl porphyrin tetrasulfonate (TPPS), zinc tetraphenyl porphyrin tetrasulfonate (ZnTPPS), ruthenium trisbipyridine, and chlorophyll.

[20] The hydrogen production reaction unit of any one of [16] to [19], wherein the artificial electron carrier is a viologen compound or a bipyridinium salt derivative.

[21] The hydrogen production reaction unit of [20], wherein the viologen compound is a compound of the formula (10).

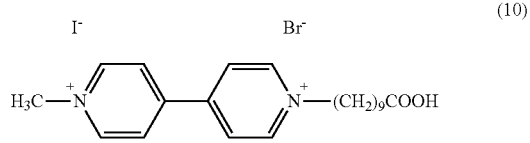

(10)

[22] The hydrogen production reaction unit of any one of [16] to [21], wherein the hydrogenase is derived from any one selected from the group consisting of genus *Ralstonia*, genus *Clostridium*, hydrogen bacteria, sulfate-reducing bacteria, cyano bacteria, and algae.

[23] The hydrogen production reaction unit of any one of [16] to [21], wherein the hydrogenase is derived from genus *Ralstonia*.

[24] A hydrogen production reactor including the hydrogen production reaction unit and a liquid phase retainer which retains a liquid containing an electron donor, wherein the liquid phase retainer is provided on the region in which a hydrogenase, an artificial electron carrier and a photosensitizer are immobilized in the insoluble support of the hydrogen production reaction unit.

[25] A method for producing hydrogen, including a step of applying light under conditions where an electron donor is fed to the hydrogen production reaction unit of any one of [16] to [23].

BRIEF DESCRIPTION OF DRAWING

FIG. 1 shows the reaction catalyzed by formate dehydrogenase (FDH) (upper row) and the time change of NADH and the concentration of formic acid (lower row). 2.2 mM of formic acid, 2.2 mM of $NAD^+$, and 5.0 units of FDH were incubated, and NADH was detection (lower row, left). On the other hand, 2.2 mM of $CO_2$, 2.2 mM of NADH, and 5.0 units of FDH were incubated, and formic acid was detected (lower row, right).

FIG. 2 shows the reaction using an artificial coenzyme having a bipyridine skeleton (upper row), and the time change of NADH and the concentration of formic acid (lower row). 2.2 mM of formic acid, 4.4 mM of methylviologen ($MV^{2+}$ was used), and 5.0 units of FDH were incubated, and NADH was detected (lower row, left). On the other hand, 2.2 mM of $CO_2$, 4.4 mM of $MV^{2+}$ chemically reduced with sodium dithionate, and 5.0 units of FDH were incubated, and formic acid was detected (lower row, right).

FIG. 3 shows the overview of an optically driven carbon dioxide-methanol conversion system. The reduction reaction by three kinds of dehydrogenase (FDH, AldDH, and ADH) is continuously promoted, whereby carbon dioxide is converted into formic acid, formic acid is converted into formaldehyde, and then formaldehyde is converted into methanol, successively. This example uses methylviologen ($MV^{2+}$) as an electron carrier.

FIG. 4 shows examples of modification of the structure of an artificial coenzyme. Methyl viologen was modified so as to increase anionic or cationic property.

FIG. 5 shows the structure of various artificial coenzymes.

FIG. 6 shows the overview of the experimental methods. The reduction potential was measured by cyclic voltammetry (upper). On the other hand, the reaction speed of formic acid was evaluated using ionic chromatography (lower).

FIG. 7 shows the reduction potential of artificial coenzymes.

FIG. 8 shows the formation of formic acid by the artificial coenzymes.

FIG. 9 summarizes the experimental results. The structure, positive charge, reduction potential, and formation of formic acid of the artificial coenzymes were compared.

FIG. 10 shows the chemical structure of tetraphenyl porphyrin tetrasulfonate (TPPS).

FIG. 11 shows the chemical structure of a viologen compound.

FIG. 12 shows the chemical structure of carboxydodecanethiol.

FIG. 13 shows the absorbance before and after immersion in TPPS and the viologen compound.

FIG. 14 shows the adsorption amount of TPPS and the viologen compound.

FIG. 15 shows an example of the structure of a reactor for solar hydrogen production.

FIG. 16 shows the state of the substrate surface fore applying visible light (upper) and after one hour (lower).

FIG. 17 shows the temporal change of the light hydrogen production reaction using a TPPS-viologen compound-hydrogenase immobilization substrate.

FIG. 18 shows the scheme of the hydrogen production reaction.

DESCRIPTION OF EMBODIMENT

A first aspect of the present invention relates to a reaction method using oxidoreductase. The reaction method of the present invention includes "the reaction catalyzed by an oxidoreductase using an artificial electron carrier". According to the present invention, a reverse redox reaction is selectively promoted. More specifically, an oxidation-reduction reaction can be controlled. In the present description, "reverse reaction" is the reverse of the main reaction (forward reaction) of the oxidoreductase. For example, for an enzyme classified into dehydrogenases, the reaction depriving hydrogen ions from the coenzyme, and giving the deprived hydrogen ion to the substrate corresponds to the reverse reaction. The present invention is applicable to, for example, production of formic acid and methanol.

"Oxidoreductase" is the generic name of the enzymes catalyzing oxidation-reduction reaction. Oxidoreductases are classified into, for example, dehydrogenases and oxidases (oxidase and reductases), based on their mechanism action and reaction products.

In the present invention, NAD (nicotinamide adenine dinucleotide)-dependent oxidoreductases are preferably used. NAD-dependent enzymes use NAD as a cofactor (coenzyme). In a natural state, NAD is essential for the expression of the activity of NAD-dependent enzymes. Examples of the NAD-dependent oxidoreductases include formate dehydrogenase (FDH), aldehyde dehydrogenase (AldDH), alcohol dehydrogenase (ADH), lactate dehydrogenase (LDH), and glutamate dehydrogenase.

The reaction conditions may be common reaction conditions suitable to the enzyme used. For example, the reaction conditions for formate dehydrogenase include a temperature of 20° C. to 65° C., pH5 to 10, those for aldehyde dehydrogenase include a temperature of 20° C. to 70° C., a pH of 4 to 10, and those for alcohol dehydrogenase include a temperature of 0° C. to 95° C., and a pH of 2 to 12. Preferred reaction conditions include a temperature of 20° C. to 40° C., and a pH of 7.0 to 8.5.

The reaction conditions suitable for the enzyme used may be established with reference to past reports and publications (for example, Yutaka Amao, Photochemistry, 42, 107 (2011).). In addition, those skilled in the art can easily find optimum reaction conditions through preliminary experiments.

According to one embodiment of the present invention, a viologen compound or a bipyridinium salt derivative is used as the electron carrier, whereby reverse redox reaction is selectively promoted. More specifically, the most important feature of the present invention is that a viologen compound or a bipyridinium salt derivative is used as an artificial coenzyme in place of the original coenzyme (cofactor). The viologen compound is a common name of N,N'-disubstituted-4,4'-bipyridinium prepared by introducing substituents into the two pyridine ring nitrogen atoms of 4,4'-bipyridine. The introduction of the substituents charges the ring nitrogen atoms positively, so that the compound works as an electron carrier. The bipyridinium salt derivative preferably has two chloride ions or bromide ions as counter ions.

The viologen compound may be the compound represented by the formula (1):

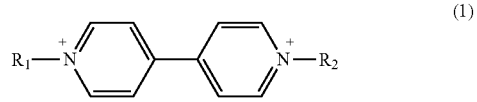

wherein R1 and R2 are each independently a substituted or unsubstituted alkyl group, a substituted or unsubstituted aryl group, or a substituted or unsubstituted arylalkyl group, and the substituted or unsubstituted alkyl group has 1 to 12 carbon atoms, substituted or unsubstituted aryl group has 6 to 20 carbon atoms, and substituted or unsubstituted arylalkyl group has 7 to 20 carbon atoms.

On the other hand, the bipyridinium salt derivative may be the compound represented by the formula (2):

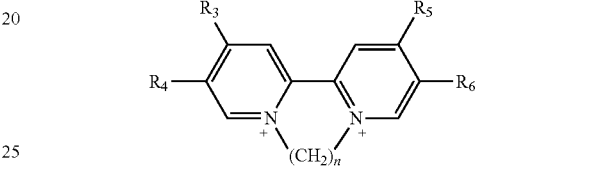

wherein R3, R4, R5, and R6 are each independently a substituted or unsubstituted alkyl group, a substituted or unsubstituted aryl group, or a substituted or unsubstituted arylalkyl group, the substituted or unsubstituted alkyl group has 1 to 12 carbon atoms, substituted or unsubstituted aryl group has 6 to 20 carbon atoms, and substituted or unsubstituted arylalkyl group has 7 to 20 carbon atoms.

In the compound represented by the formula 1 or 2, the substituent in the alkyl group, aryl group, or arylalkyl group is, for example, a substituted or unsubstituted amino group, carboxyl group, t-butyl group, or benzyl group. Examples of the substituted amino group include a methylamino group, a dimethylamino group, an ethylamino group, a diethylamino group, an n-propylamino group, a di-n-propylamino group, an isopropylamino group, a diisopropylamino group, an n-butylamino group, a di-n-butylamino group, a sec-butylamino group, a di-sec-butylamino group, a tert-butylamino group, a di-tert-butylamino group, an n-pentylamino group, a 2,2-dimethylpropylamino group, an n-hexylamino group, a cyclohexylamino group, an n-heptylamino group, an n-octylamino group, an n-nonylamino group, an n-decylamino group, an n-undecylamino group, an n-dodecylamino group, an n-tridecylamino group, an n-tetradecylamino group, an n-pentadecylamino group, an n-hexadecylamino group, an n-heptadecylamino group, an n-octadecylamino group, an n-nonadecylamino group, an n-icosylamino group, a pyrrolyl group, a pyrrolidinyl group, a piperidinyl group, a carbazolyl group, a dihydroindolyl group, and a dihydroisoindolyl group.

According to a preferred embodiment, the compound represented by the formula (3) is used as the viologen compound:

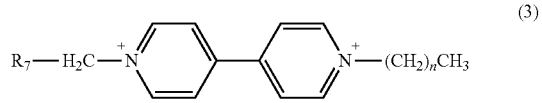

wherein n is an integer of 0 to 10, R7 is a hydrogen atom, a methyl group, a substituted or unsubstituted amino group, an aminomethylene group, a carboxyl group, a t-butyl group, or a benzyl group.

According to another preferred embodiment, the compound represented by the formula (4) is used as the bipyridinium salt derivative:

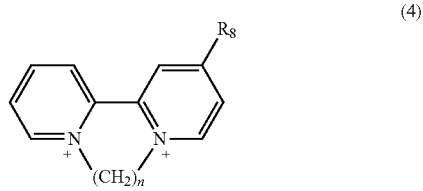

(4)

wherein n is an integer of 1 to 10, R8 is a methyl group, a substituted or unsubstituted amino group, a carboxyl group, a t-butyl group, or a benzyl group.

Specific examples of the viologen compound used in the present invention are shown by the following formulae (5) to (9):

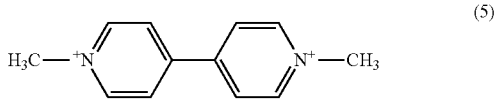

(5)

(1,1'-dimethyl-4,4'-bipyridinium, Synonym(s): methylviologen)

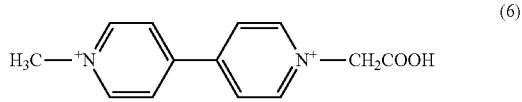

(6)

(1-methyl-1'-carboxylmethyl-4,4'-bipyridine)

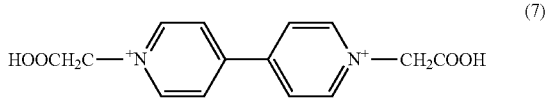

(7)

(1,1'-dicarboxymethyl-4,4'-bipyridine)

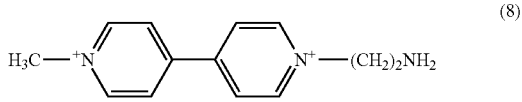

(8)

(1-methyl-1'-aminoethyl-4,4'-bipyridine)

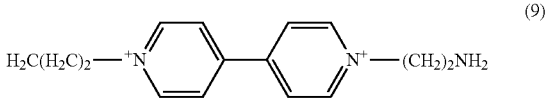

(9)

(1,1'-diaminoethyl-4,4'-bipyridine)

As shown by the below-described examples, the compounds with cationic structures represented by the formulae (8) and (9) are specifically useful, because they have high affinity for enzymes, or readily interact with enzymes. Accordingly, these compounds are preferably used. Specific examples of the viologen compound besides the above-described compounds (the formulae (5) to (9)) include 1,1'-dibenzyl-4,4'-bipyridinium, 1,1'-dihexyl-4,4'-bipyridinium, 1,1'-diheptyl-4,4'-bipyridinium, 1,1'-dinonyl-4,4'-bipyridinium, 1,1'-didecyl-4,4'-bipyridinium, 1,1'-bis(2,4-dinitro phenyl)-4,4'-bipyridinium dichloride, 1,1'-dibenzyl-4,4'-bipyridinium dichloride hydrate (benzyl viologen), 1,1'-diheptyl-4,4'-bipyridinium dibromide, 1,1'-dimethyl-4,4'-bipyridinium dichloride (methylviologen), 1,1'-di-n-octyl-4,4'-bipyridinium dibromide, and 1,1'-diphenyl-4,4'-bipyridinium dichloride. Two or more of these compounds may be used together.

The reaction method of the present invention typically includes the following steps (1) and (2):

(1) a step of reducing the electron carrier, and forming a reduced electron carrier; and (2) a step of allowing the oxidoreductase to act to the substrate in the reverse reaction in the presence of the reduced electron carrier thus formed.

In the step (1), the electron carrier (viologen compound or bipyridinium salt derivative) is reduced, and a reduced electron carrier is formed. In order to reduce the electron carrier, a reducing agent is allowed to act on the electron carrier. More specifically, for example, a state of coexistence of the electron carrier and reducing agent is created in a solution where the reaction occurs. Various reducing agents may be used. Examples of the reducing agent include sodium dithionate, sodium dithionite, ascorbic acid, and hydrazine. Among them, sodium dithionate, sodium dithionite, and hydrazine are preferred, sodium dithionate and sodium dithionite are more preferred, and sodium dithionate is most preferred.

On the other hand, the electron carrier may be reduced by application of light under the coexistence of the electron donor and photo sensitizer. This method using light energy is particularly effective for the establishment of a circulated reaction system. Any electron carrier and photosensitizer may be used as long as the combination reduces the electron carrier. Various compounds having an electron-donating group may be used as the electron donor. Examples of the electron donor include triethanolamine, ethylenediamine, ethylenediamine-tetraacetic acid salt, ethylenediamine hydrochloride, triethylamine, and mercaptoethanol. Examples of the photosensitizer include a porphyrin derivative, a ruthenium bipyridine complex derivative, a pyrene derivative, and a chlorophyll derivative, such as zinc tetrakis (4-methylpyridyl) porphyrin (ZnTMPyP), zinc tetraphenyl porphyrin tetrasulfonate (ZnTPPS), ruthenium trisbipyridine, and chlorophyll.

In the step (2), oxidoreductase is allowed to act on the substrate in the reverse reaction of oxidoreductase in the presence of the reduced electron carrier formed in the step (1). In order to carry out this step, for example, a state of coexistence of the reduced electron carrier thus formed, oxidoreductase, and substrate is formed in the solution where reaction occurs, and then the solution is incubated under conditions suitable for enzymatic reaction. The reaction time may be appropriately set according to the intended use, and, for example, from 1 to 48 hours.

The reaction method of the present invention may be carried out as, for example, enzymatic reaction catalyzed by formate dehydrogenase (hereinafter may be carried out as "the formic acid formation method of the present invention"). More specifically, a specific embodiment of the reaction method of the present invention is the method of converting carbon dioxide into formic acid, including carrying out the enzymatic reaction catalyzed by formate dehydrogenase in the presence of carbon dioxide, using a viologen compound or a bipyridinium salt derivative as the electron carrier. In this method, as the step (2), for example, a state of coexistence of formate dehydrogenase, a reduced electron carrier (a viologen compound or a bipyridinium salt derivative), and carbon dioxide is created in a solution, and formate dehydrogenase is allowed to act on carbon dioxide. The origin of the formate dehydrogenase is not particularly limited. Examples of the formate dehydrogenase include those derived from microorganisms known to express formate dehydrogenase, such as *Achromobacter parvulus, Ancylobacter aquaticus, Arthrobacter* sp. *Candida methanolica, Candida methylica, Clostridium acidurici, Cupriavidus necator, Cupriavidus oxalaticus, Cupriavidus oxalaticus, Desulfovibrio desulfuricans, Escherichia coli, Gelatoporia subvermispora, Glycine max, Hyphomicrobium* sp., *Kloeckera* sp., *Lotus japonicus, Methylophilus methylotrophus, Methylosinus trichosporium, Methylococcus capsulatus, Methylobacterium organophilum, Methylobacterium extorquens, Moraxella* sp., *Mycobacterium vaccae, Ogataea pini, Paracoccus denitrificans, Paracoccus* sp., *Pichia angusta, Pichia pastoris, Pisum sativum, Pseudomonas methylica, Rhodopseudomonas palustris, Saccharomyces cerevisiae, Thiobacillus* sp., and *Torulopsis candidaVigna radiata* var. *radiata*. Among them, formate dehydrogenase derived from *Candida boidinii* (for example, commercially available from Roche Applied Science and Sigma-Aldrich) is preferably used. In addition to wild type enzymes, recombinant enzymes are also useful.

A second aspect of the present invention is an application of the first aspect, and relates to a method for producing methanol from carbon dioxide (hereinafter referred to as "methanol production method of the present invention"). One embodiment of the methanol production method of the present invention includes the following steps (i) and (ii):

(i) a step of an allowing an aldehyde dehydrogenase to act on the formic acid, which has formed by the formic acid formation method of the present invention, using a viologen compound or a bipyridinium salt derivative as an electron carrier, thereby converting formic acid into formaldehyde; and (ii) a step of allowing an alcohol dehydrogenase to act on the formaldehyde, which has been formed by the step (i), using a viologen compound or a bipyridinium salt derivative as an electron carrier, thereby converting formaldehyde into methanol.

In the step (i) of the present invention, formaldehyde is obtained using the formic acid, which has been formed by the above-described formic acid formation method, as the substrate. Accordingly, in the present invention, a viologen compound or a bipyridinium salt derivative is used as an artificial coenzyme (electron carrier) in place of the natural coenzyme, and enzymatic reaction (reverse reaction) by aldehyde dehydrogenase is carried out. Details about the electron carrier are the same as those in the first aspect, but the electron carrier used for the formation of formic acid and the electron carrier in the step (i) may be different. In this case, a first electron carrier is used for the formation of formic acid, and a second electron carrier different from the first electron carrier is used in the step (i). The second electron carrier herein is preferably methylviologen, the compound represented by the formula (8), or the compound represented by the formula (9).

The electron carrier in the step (i) is preferably the same compound as the electron carrier used for the formation of formic acid. This embodiment allows the construction of a more simple reaction system, and carrying out a series of reaction in the same reaction solution (formation of formic acid from carbon dioxide, and subsequent formation of formaldehyde from formic acid). When a series of reaction is carried out in the same reaction liquid, there are two cases: the reaction by formate dehydrogenase is initiated under the coexistence of formate dehydrogenase and aldehyde dehydrogenase in the reaction solution; or the reaction by formate dehydrogenase is initiated in the absence of aldehyde dehydrogenase in the reaction solution, and then aldehyde dehydrogenase is added after the lapse of a predetermined time (for example, 30 minutes to 24 hours). In the former case, it is not necessary to add aldehyde dehydrogenase in midstream (alternatively, the aldehyde dehydrogenase may be added in the later stage for the purpose of replenishing deficient enzyme), which simplify the procedure. On the other hand, the latter case allows the control of the initiation point of the reaction by aldehyde dehydrogenation.

In the step (ii), which follows the step (i), methanol is obtained using the formaldehyde formed in the step (i) as the substrate. Therefore, in the present invention, in the same manner as in the step (i), a viologen compound or a bipyridinium salt derivative is used as an artificial coenzyme (electron carrier) in place of a natural coenzyme, and enzymatic reaction (reverse reaction) by alcohol dehydrogenase is carried out. Details about the electron carrier are the same as in the first aspect, but the electron carrier used in the formation of formic acid or the electron carrier used in the step (i) may be different from the electron carrier in the step (ii). For example, the first electron carrier is used in the formation of formic acid, the second electron carrier is used in the step (i), and the third electron carrier different from these two electron carriers may be used in the step (ii). Alternatively, the same electron carrier is used in the formation of formic acid and the step (i), and a different electron carrier is used in the step (ii) alone. Also in the step (ii), preferably, methylviologen, the compound represented by the formula (8), or the compound represented by the formula (9) is used as the electron carrier.

Preferably, the same electron carrier is used in the formation of formic acid and the steps (i) and (ii). This embodiment allows to establish a more simple reaction system, and to carry out a series of reaction in the same reaction solution (formation of formic acid from carbon dioxide, formation of formaldehyde from formic acid, and formation of methanol from formaldehyde). The steps (i) and (ii) may use two or more electron carriers in the same manner as in the formation of formic acid.

In order to simplify the operation, it is preferred that the reaction by formate dehydrogenase be initiated under conditions where all the three enzymes coexist. Alternatively, aldehyde dehydrogenase and alcohol dehydrogenase may be added in the later stage, or alcohol dehydrogenase alone may be added in the subsequent step.

According to another embodiment of the present invention, the following steps (1) and (2) are carried out, thereby methanol is produced from carbon dioxide:

(1) a step of forming the conditions where formate dehydrogenase, aldehyde dehydrogenase, alcohol dehydrogenase, a viologen compound, or a bipyridinium salt derivative, an electron donor, a photosensitizer, and carbon dioxide coexist in a solution; and (2) a step of applying light to the solution.

This embodiment is an optically driven carbon dioxide-methanol conversion reaction system, wherein the reaction by formate dehydrogenase (formation of formic acid from carbon dioxide), the reaction by aldehyde dehydrogenase (formation of formaldehyde from formic acid), and the reaction by alcohol dehydrogenase (formation of methanol from formaldehyde) successively proceed, using the electron carrier, which has been reduced by light energy, as the artificial coenzyme. As a result of this, methanol is formed as the end product. Details about the formate dehydrogenase, aldehyde dehydrogenase, alcohol dehydrogenase and electron carrier (viologen compound or bipyridinium salt derivative) are the same as those described above, so that detailed explanations thereof will be omitted.

The electron donor (donor) may be selected from various compounds having an electron-donating group. Examples of the electron donor include triethanolamine, ethylenediamine, ethylenediamine-tetraacetic acid salt, ethylenediamine hydrochloride, triethylamine, and mercaptoethanol.

The photosensitizer is also not particularly limited, and examples thereof include porphyrin derivatives, ruthenium bipyridine complex derivatives, and pyrene derivatives, such as zinc tetrakis(4-methylpyridyl) porphyrin (ZnTMPyP), zinc tetraphenyl porphyrin tetrasulfonate (ZnTPPS), ruthenium trisbipyridine, and chlorophyll.

The coexistence of the enzymes, electron carrier, electron donor, photosensitizer, and carbon dioxide is formed before photoirradiation. Accordingly, the order and method of adding these components are not particularly limited. For example, according to one embodiment, the step (1) includes the following steps (1-1) and (1-2):

(1-1) a step of adding formate dehydrogenase, aldehyde dehydrogenase, alcohol dehydrogenase, a viologen compound or a bipyridinium salt derivative, an electron donor, and a photosensitizer to the solvent; and (1-2) a step of feeding carbon dioxide to the solution obtained in the step (1-1).

The solvent in the step (1-1) is not particularly limited as long as the enzymatic reactions proceed therein. For example, buffer solutions such as a pyrophosphate buffer solution, a phosphate buffer solution, a citrate buffer solution, or an acetate buffer solution may be used. The pH of the reaction solution is, for example, from 5 to 10, and preferably from 7.0 to 8.5.

The feeding of carbon dioxide to the step (1-2) is carried out by, for example, aeration, bubbling into the solution, gas phase substitution, or addition of a carbonate. The steps (1-2) and (2) may be carried out in parallel. More specifically, light may be applied while feeding carbon dioxide. In addition, feeding of carbon dioxide may be continued after photoirradiation. The manner of feeding may be single feeding, plural times of (intermittent) feeding, continuous feeding, or the combination of the latter two manners.

According to another embodiment, the following steps (1-3) to (1-5) are carried out as the step (1):

(1-3) a step of adding aldehyde dehydrogenase, alcohol dehydrogenase, a viologen compound or a bipyridinium salt derivative, an electron donor, and a photosensitizer to the solvent;

(1-4) a step of feeding carbon dioxide to the solution obtained in the step (1-3); and (1-5) a step of adding formate dehydrogenase to the solution after the step (1-4).

This embodiment is featured in that the formate dehydrogenase catalyzing the first reaction is added last. This feature allows easy control of the time of reaction initiation. The components in the step (1-3), the method for feeding carbon dioxide (step (1-4)), and formate dehydrogenase are the same as those in the above-described embodiment, so that detailed explanations thereof are omitted. Carbon dioxide may be fed again after initiation of the reaction (more specifically, the step (2) following the step (1-5)).

In the step (2), which follows the step (1), light is applied to the solution in which necessary components coexist (more specifically, a solution containing formate dehydrogenase, aldehyde dehydrogenase, alcohol dehydrogenase, a viologen compound or a bipyridinium salt derivative, an electron donor, a photosensitizer, and carbon dioxide). The type of the light source is not particularly limited as long as it can excite the photosensitizer. Various light sources may be used. Examples of the light source include a cold-cathode tube, a fluorescent lamp, a mercury lamp, a halogen lamp, an ultraviolet lamp, an LED lamp, LED laser, and an EL (electroluminescence) light.

Another aspect of the present invention relates to a hydrogen production reaction unit and the use thereof. The "hydrogen production reaction unit" is a structure for carrying out a series of reaction for producing hydrogen, and includes an insoluble support, hydrogenase, an artificial electron carrier, and a photosensitizer.

The hydrogenase, artificial electron carrier, and photosensitizer are immobilized on the insoluble support. The hydrogenase, artificial electron carrier, and photosensitizer are immobilized in the same region on the insoluble support, thereby a series of giving and receiving (communication) of electrons is caused. Typically, a part of region of the insoluble support is used as the reaction region, and the hydrogenase, artificial electron carrier, and photosensitizer are immobilized in the region. Alternatively, the whole surface of the insoluble support may be used as the immobilization region.

The insoluble support is a substance insoluble in water, and examples thereof include resins such as a polystyrene resin, a polycarbonate resin, a silicon resin, or a nylon resin, metals, semiconductors, ceramic, and glass. The material is not particularly limited, and the shape of the insoluble support is also not particularly limited. For example, an insoluble support formed into a plate, sphere, or rod may be used.

The immobilization method is not particularly limited. For example, the components (hydrogenase, an artificial electron carrier, and a photosensitizer) are immobilized on the insoluble support by adsorption or chemical bonding. As shown in the below-described examples, these components may be immobilized by embedding or coating using a gel material or the like.

Hydrogenase is an enzyme catalyzing hydrogen oxidative reaction and proton reduction reaction. In the present invention, the reaction forming hydrogen ($H_2$), more specifically, proton reduction reaction is used. Examples of hydrogenase include those derived from genus *Ralstonia* (for example, Van der Linden, E., T. Burgdorf, A. L. de Lacey, T. Buhrke, M. Scholte, V. M. Fernandez, B. Friedrich, and S. P. Albracht. 2006. An improved purification procedure for the soluble [NiFe]-hydrogenase of *Ralstonia eutropha*: new insights into its (in) stability and spectroscopic properties. See J Biol Inorg Chem. 11: 247-60), those derived from hydrogen bacteria (for example, see Japanese Unexamined Patent Application Publication No. 2000-350585), those derived from sulfate-reducing bacteria (for example, see J Biosci BioEng. 2013 April; 115(4): 366-71.), those derived from cyano bacteria (for example, see J Biol Chem. 2009 Dec. 25; 284(52): 36462-72.), those derived from algae (for example, see Plant Physiol. 1984 July; 75(3): 705-9.), and those derived from genus *Clostridium* (for example, see Methods Enzymol. 1978; 53: 286-96). According to a preferred embodiment, hydrogenase derived from genus *Ralstonia* is used. The hydrogenase may be prepared with reference to the above-described literature (reference by Van der Linden, E. et al.) and the reference by Schneider, K., et al. (Schneider, K., and H. G. Schlegel. 1976. Purification and properties of the soluble hydrogenase from *Alcaligenes eutrophus* H16. Biochim. Biophys. Acta 452: 66-80.). According to an example of the preparation method, the bacterial cells after culture are fractured, the supernatant is collected, and purified by a DEAE-Sepharose column and a Phenyl-Sepharose column, thereby obtaining a purified enzyme.

The artificial electron carrier may be a viologen compound or a bipyridinium salt derivative. Details about the viologen compound or bipyridinium salt derivative are the same as those described above, so that repetitive explanations thereof will be omitted. According to a preferred embodiment of this aspect, the viologen compound represented by the formula (10) is used as the artificial electron carrier:

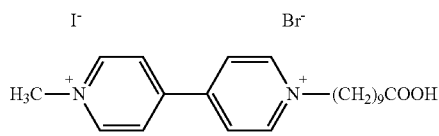

The photosensitizer may be a porphyrin derivative, a ruthenium bipyridine complex derivative, a pyrene derivative, or a chlorophyll derivative. Specific examples include zinc tetrakis (4-methylpyridyl) porphyrin (ZnTMPyP), tetraphenyl porphyrin tetrasulfonate (TPPS), zinc tetraphenyl porphyrin tetrasulfonate (ZnTPPS), ruthenium trisbipyridine, and chlorophyll.

When hydrogen is produced using the hydrogen production reaction unit of the present invention, light is applied under conditions where an electron donor is fed. A liquid containing an electron donor is used for feeding the electron donor. The liquid is exposed to the insoluble support region composing the hydrogen production reaction unit in the region where hydrogenase, an artificial electron carrier, and a photosensitizer are immobilized, whereby the electron donor is fed. The electron donor used herein is the same as that in the above-described aspect, so that corresponding explanation is incorporated herein, and repetitive explanation thereof will be omitted. On the other hand, the type of the light source is not particularly limited. Various light sources may be used. Typically, sunlight is used. Alternatively, artificial light sources such as a cold-cathode tube, a fluorescent lamp, a mercury lamp, a halogen lamp, an ultraviolet lamp, an LED lamp, an LED laser, or an EL (electroluminescence) light may be used.

The application of light in the presence of the electron donor excites the photosensitizer, electrons are moved from the excited photosensitizer to the electron carrier, the electron carrier which has received the electrons is reduced, and then a reduced electron carrier is formed. The reduced electron carrier feeds electrons to the hydrogenase. As a result of this, enzymatic reaction is promoted, and protons are reduced to form hydrogen (see FIG. 18).

A hydrogen production reactor can be constructed using the hydrogen production reaction unit of the present invention. The use of the hydrogen production reactor is suitable to, for example, efficient and/or large-scale production of hydrogen. The hydrogen production reactor includes a hydrogen production reaction unit and a liquid phase retainer which retains a liquid containing an electron donor. The liquid phase retainer is provided on the region in which a hydrogenase, an artificial electron carrier and a photosensitizer are immobilized in the insoluble support of the hydrogen production reaction unit. The liquid phase retainer may be composed of, for example, a division plate and a channel. It may include a cabinet, a means for feeding a liquid phase (for example, a pump and a channel), a means for collecting the hydrogen produced (for example, a channel and a pressurizer), and a space for temporarily retaining the hydrogen produced. In addition, it may further include a light source (in a case where a light source other than sunlight is used).

[Example]

1. Study of Reaction Properties of Formate Dehydrogenase (FDH)

The enzyme catalyzing the reaction converting formic acid into carbon dioxide, "formate dehydrogenase (FDH)" also catalyzes the reaction converting carbon dioxide into formic acid. It should be noted that the speed of the conversion reaction from carbon dioxide into formic acid (reverse reaction) is about one sixth the speed of the conversion reaction from formic acid into carbon dioxide (forward reaction) (FIG. 1). Suppression of the forward reaction is important for the formation of formic acid from carbon dioxide using this enzyme. The original coenzyme of FDH is $NAD^+$, but methylviologen may be used as an artificial coenzyme (mediator) (Non-Patent Literature 2). However, in the past report, only the interaction between FDH and methylviologen is electrochemically measured, so that no essential finding about the interaction is obtained. Therefore, we studied the characteristics of the FAD reaction system using methylviologen as an artificial coenzyme in detail. As a result of this, surprisingly, the conversion reaction from formic acid into carbon dioxide does not proceed at all, but the conversion reaction from formic acid into carbon dioxide only proceeds (FIG. 2). More specifically, it was found that the use of methylviologen allows markedly selective promotion of reverse reaction. Methylviologen is advantageous also in that it is readily photoreduced using a photosensitive molecule. In contrast, photoreduction of the original coenzyme, $NAD^+$ is not easy.

2. Study for the Improvement of Reaction Efficiency

The study group of the inventors reported the optically driven carbon dioxide-methanol conversion system using three dehydrogenases (FDH, AldDH, and ADH) (Non-Patent Literature 1. see FIG. 3). Methylviologen is useful as a mediator of FDH (electron carrier) (see above), and is also useful as a mediator of AldDH and ADH. In the optically driven carbon dioxide-methanol conversion system using methylviologen as the mediator, methylviologen is photoreduced by light energy, and carbon dioxide is converted into methanol through formic acid and formaldehyde by the reaction of three dehydrogenases. These enzymes recognize reduced methylviologen alone as the substrate, which allows to take out only the necessary reaction of the reversible reaction (i.e. reverse reaction) seen when the natural coenzyme $NAD^+$ is used. Accordingly, selective and effective reaction is achieved.

In order to increase the formation efficiency of methanol, the increase of the conversion efficiency from carbon dioxide into formic acid is most important and effective. Therefore, for the purpose of improvement of the efficiency of the conversion reaction from carbon dioxide into formic acid, which is the most important step of methanol formation, artificial coenzymes composed of a bipyridinium salt and various ionic substituents were synthesized (FIGS. 4 and 5), and the correlation between the chemical structure and function of the artificial coenzymes in the carbon dioxide-formic acid conversion reaction using FDH was studied.

(1) Material and Method (1-1) Synthesis and Electrochemical Properties of Artificial Coenzymes The chemical structure of the synthesized artificial coenzymes composed basically of 4,4'-bipyridine (BP) in FIG. 5.

Hereinafter, methylviologen is defined as $MV^{2+}$, 1-methyl-1'-carboxylmethyl-4,4'-bipyridine as artificial coenzyme A, 1,1'-dicarboxymethyl-4,4'-bipyridine as artificial coenzyme B, 1-methyl-1'-aminoethyl-4,4'-bipyridine as artificial coenzyme C, and 1,1'-diaminoethyl-4,4'-bipyridine as artificial coenzyme D, respectively (FIG. 5). The reduction potential of the synthesized artificial coenzymes was measured by cyclic voltammetry (working electrode: glassy carbon electrode, reference electrode: silver chloride electrode, counter electrode: platinum wire electrode) (FIG. 6).

(1-2) Carbon Dioxide-formic Acid Conversion Reaction Using FDH

The conditions of the carbon dioxide-formic acid conversion reaction are as follows. 2.0 ml of a pH 7.4 sodium pyrophosphate buffer solution (50 mM) containing 1.5 ml of an artificial coenzyme (2 mM) and 0.1 ml of FDH (10 units/ml), which had been thoroughly vacuum-deaerated to substitute the gas phase with nitrogen, was mixed with sodium dithionate (5.7 mmol) in a quartz cell while $CO_2$ gas was introduced, and incubated at a reaction temperature of 30.5° C. The concentration of formic acid 1 minute after initiation of the reaction was determined by ion chromatograph (FIG. 6).

(2) Result (2-1) Synthesis and Electrochemical Properties of Artificial Coenzymes The reduction potentials of the synthesized artificial coenzymes determined from cyclic voltammogram are shown in FIG. 7. The reduction potentials of the artificial coenzymes synthesized herein were from −0.60 to −0.67 V, which are almost the same as that of $MV^{2+}$. This fact means that the introduction of a substituent into 4,4'-bipyridine does not markedly influence the oxidation-reduction potential.

(2-2) Carbon Dioxide-formic Acid Conversion Reaction Using Artificial Coenzyme and FDH The carbon dioxide-formic acid conversion reaction using an artificial coenzyme and FDH was studied. The result of the comparison of the formic acid concentration 1 minute after initiation of the reaction is shown in FIG. 8. With reference to $MV^{2+}$, the formation of formic acid increased when the artificial coenzymes C and D, which have higher positive charges due to the addition of cationic amino groups, were used. On the other hand, the formation of formic acid decreased when the artificial coenzymes A and B having anionic carboxy groups were used. In consideration that the oxidation-reduction potentials of the artificial coenzymes are not so different, the formation of formic acid in this reaction system depends on the chemical structure of the artificial coenzyme, the interaction with FDH is strengthened when the artificial coenzyme has more cationic chemical structure, which likely accelerated the carbon dioxide-formic acid reaction. The relationship between the structure, positive charge, reduction potential of the artificial coenzymes, and the formation of formic acid is summarized in FIG. 9.

(3) Discussion

Studies for changing the structure of enzymes to enzymatic activity have been carried out, but there is little study regarding the chemical structure of artificial coenzymes and enzymatic activity, and suppression of reaction. The findings obtained by this study are expected to bring about new development of future technology for using enzymes.

3. Construction of Hydrogen Production Reaction System

In recent years, global environmental problems such as the increase of carbon dioxide are growing. Therefore, it is immediately necessary to develop energy replacing fossil fuels such as petroleum and coal, which cause the increase of carbon dioxide. Accordingly, at present, systems for obtaining hydrogen by decomposing water are receiving attention. The study group of the inventors has established a hydrogen photoproduction reaction system composed of an electron donor, a photosensitizer, an electron carrier, and a catalyst. Described below is the study on a new hydrogen production reaction system for the improvement of the efficiency of hydrogen production, the system including a substrate on which a photosensitizer, an electron carrier and a hydrogenase as a catalyst are immobilized 3-1. Making of Substrate Immobilizing TPPS-viologen Compound-hydrogenase The TPPS-viologen compound-hydrogenase immobilizing substrate was made as follows.

(1) Reagent

Tetraphenyl porphyrin tetrasulfonate ($C_{44}H_{30}N_4O_{12}S_4$=934.99) was purchased from Tokyo Chemical Industry Co., Ltd. A viologen compound ($C_{21}H_{30}O_2IBr$=520.8) was synthesized and used. 10-carboxy-1-decanethiol ($C_{11}H_{22}O_2S$=218.36) was purchased from Dojindo Laboratories. The enzyme hydrogenase was derived from genus *Ralstonia*. The pH 6.86 neutral phosphate buffer solution, polylysine, and polyglutamic acid were purchased from Wako Pure Chemical Industries, Ltd. The structures of TPPS, the viologen compound, and carboxydecanethiol are shown in FIGS. 10 to 12.

(2) Preparation of Reaction Solution

TPPS, the viologen compound, and carboxydecanethiol were individually dissolved in methanol, and adjusted to 40 µM, 50 µM, and 50 µM, respectively.

(3) Making of TPPS-viologen Compound Immobilizing Substrate

A TLC plate (silica gel plate) of 2.8×1.4 cm was provided, immersed in a 0.01 M hydrochloric acid solution for 30 minutes, the both sides were washed with RO water, and dried. The TLC plate treated with hydrochloric acid was immersed in 1.7 ml of the TPPS, viologen compound, and carboxydecanethiol solutions, which had been prepared under conditions descried in [0069], for 1 hour in a constant temperature bath at 30° C. After the immersion, 15 ml of methanol was circulated using a cassette tube pump over a period of 15 minutes, and then dried.

(4) Measurement of Adsorption Amount

The amounts of adsorption of TPPS, viologen compound on the TLC plate were calculated by measuring the absorbance of the TPPS and viologen compound solution before and after immersion of the TLC plate. The measurement used UV-VISIBLE SPECTROPHOTOMETER S-3150.

The ultraviolet-visible absorption spectra of the TPPS and viologen compound solution before and after immersion of the TLC plate are shown in FIG. 13. In addition, the amount of adsorption of the TPPS and viologen compound to the TLC plate is shown in FIG. 14. The absorptions of the TPPS and viologen compound are present at 650 nm and 260 nm, respectively.

FIGS. 13 and 14 suggest that about 20% of the TPPS and viologen compound contained in the solution was adsorbed. The adsorption amounts were higher when the solution concentration was 40 µM for TPPS and 50 µM for the viologen compound, so that these concentrations were used for the following study.

(5) Adsorption of Hydrogenase

Under the conditions shown in [0073], hydrogenase was added to the TPPS-viologen compound immobilizing substrate which had been prepared above, and dried. Thereafter, polylysine and polyglutamic acid dissolved in a neutral phosphate buffer were respectively added to the substrate, and dried to form a polyion complex thin film, thereby immobilizing hydrogenase.

3-2. Development of Reactor for Solar Hydrogen Production Reaction

In order to carry out hydrogen photoproduction reaction by application of visible light, a reactor for solar hydrogen production was made. The method for making reactor for solar hydrogen production is described below.

(1) Material

Silicon rubber (thickness 0.3 cm), glass plate, double-side tape, and clip were used.

(2) Making of Reactor for Solar Hydrogen Production Reaction

Two silicon rubber separators each having a volume of 1.4 cm$^3$ and 3.0 cm$^3$ were provided, overlaid with each other, and sandwiched between glass plates. The TPPS-viologen compound-hydrogenase adsorption substrate, which had been made in [0074], was fixed to the lower glass plate using the double-side tape. The finished drawing is shown in FIG. 15.

The reactor thus made was thoroughly deaerated with nitrogen gas, thereby preventing oxidation of the reduced viologen compound which is necessary for hydrogen photoproduction. After thorough deaeration, the lower part of the reactor for solar hydrogen production reaction was filled with a reaction solution containing triethanolamine as the electron donor. Thereafter, hydrogen photoproduction reaction by application of visible light using a solar simulator was studied.

3-3. Reduction of Viologen Compound by Application of Visible Light

In order to carry out hydrogen production reaction using the reactor for solar hydrogen production reaction, the viologen compound on the substrate must be photoreduced by application of visible light. Therefore, it was confirmed if the viologen compound on the TPPS-viologen compound immobilizing substrate was photoreduced by application of visible light.

(1) Reagent

Triethanolamine (N(CH$_2$CH$_2$OH)$_3$=149.19) was a commercial product. The neutral phosphate buffer solution with a pH of 6.86 was that described above.

(2) Preparation of Reaction Solution 14.96 g of triethanolamine was measured, dissolved in the neutral phosphate buffer solution, and then adjusted to pH 7.4 using a hydrochloric acid solution. Thereafter, the neutral phosphate buffer solution was added, and the total amount was adjusted to 100 ml, and the final concentration was adjusted to 1 M.

(3) Reduction of Viologen Compound by Application of Visible Light

The lower liquid phase of the reactor for solar hydrogen production reaction, in which the TPPS-viologen compound adsorption substrate with no hydrogenase had been fixed, was filled with the reaction solution described in [0081], and thoroughly deaerated using a nitrogen gas. Thereafter, visible light was applied from the top using a solar simulator (100 mWcm$^{-2}$).

(4) Image Analysis

In order to confirm that the viologen compound on the substrate had been photoreduced by application of visible light, the color change on the substrate surface based on photoreduction of the viologen compound region was confirmed. The substrate surface before and one hour after application of visible light was subjected to RGB analysis, and 100 optional points were integrated. The measurement used image analysis (Adobe Photoshop (registered trademark)).

The states of the substrate surface before and one hour after application of visible light are shown in FIG. 16. The colors of the substrate surface were definitely different between before and one hour after application of visible light. In addition, as a result of the RGB analysis, the proportion of green in the brightness value changed from 0.34 to 0.40. This fact shows that electrons transferred from the TPPS, which had been excited by application of visible light, to the viologen compound, whereby the viologen compound was photoreduced.

From the above-described results, it was confirmed that the viologen compound region on the TPPS-viologen compound immobilizing substrate is photoreduced by application of visible light.

3-4. Hydrogen Photoproduction Reaction Using Reactor for Solar Hydrogen Production Reaction As described above, the viologen compound on the immobilizing substrate was photoreduced by irradiation with visible light. Subsequently, using the TPPS-viologen compound-hydrogenase immobilizing substrate, hydrogen photoproduction reaction using the reactor for solar hydrogen production reaction was performed.

(1) Reagent

The triethanolamine and neutral phosphate buffer solution were the same as those described above.

(2) Preparation of Reaction Solution

The reaction solution was used.

(3) Hydrogen Photoproduction Reaction by Photoirradiation Using the Reactor for Solar Hydrogen Production Reaction The lower liquid phase of the reactor for solar hydrogen production reaction, on which the TPPS-viologen compound-hydrogenase adsorption substrate had been fixed, was filled with the reaction solution, and thoroughly deaerated using nitrogen gas. Thereafter, visible light was applied from the top using a solar simulator (100 mWcm$^{-2}$). After the initiation of application of visible light, the gas phase was collected at regular intervals, and the hydrogen formed was determined using gas chromatography (carrier gas: argon gas, detector: TCD).

The change of the formation of hydrogen with time is shown in FIG. 17. The abscissa shows photoirradiation time, and the ordinate shows the formation of hydrogen. It was confirmed that the formation of hydrogen increased with time by application of visible light. The formation of hydrogen after 5 hours of photoirradiation was 4.0 nmol.

As described above, the TPPS, viologen compound, and hydrogenase were immobilized on the same substrate, whereby a device for hydrogen photoproduction was constructed.

INDUSTRIAL APPLICABILITY

The reaction system of the present invention uses a viologen compound and the like as artificial coenzymes (mediators), and thus selectively promotes the reverse redox reaction. The application of the present invention is expected in a wide range of fields (for example, bioenergy field and biorefinery field), as a new means for altering enzyme reaction, which is different from prior art means such as the alteration of enzyme themselves using protein engineering, and adjustment of reaction conditions. In particular, the present invention is useful as a means for efficiently producing methanol from carbon dioxide.

The present invention will not be limited to the description of the embodiments and examples of the present invention. Various modifications easily by those skilled in the art are also included in the present invention, without departing from the scope of claims. The entire contents of the articles, unexamined patent publications, and patent applications specified herein are hereby incorporated herein by reference.

The invention claimed is:

1. A method for selectively promoting a reverse redox reaction, comprising:

contacting an artificial electron carrier with an electron donor and photosensitizer and applying light to form a reduced artificial electron carrier, or contacting an artificial electron carrier with a reducing agent to form a reduced artificial electron carrier, wherein the artificial electron carrier is the compound of any one of the formulae (1) to (5):

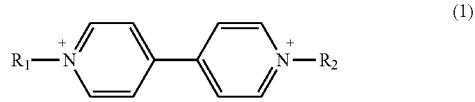
(1)

wherein R1 is a alkyl group substituted by a substituted or unsubstituted amino group, a aryl group substituted by a substituted or unsubstituted amino group, or a arylalkyl group substituted by a substituted or unsubstituted amino group, and the alkyl group has 1 to 12 carbon atoms, the aryl group has 6 to 20 carbon atoms, and the arylalkyl group has 7 to 20 carbon atoms, wherein R2 is a substituted or unsubstituted alkyl group, a substituted or unsubstituted aryl group, or a substituted or unsubstituted arylalkyl group, and the alkyl group has 1 to 12 carbon atoms, the aryl group has 6 to 20 carbon atoms, and the arylalkyl group has 7 to 20 carbon atoms,

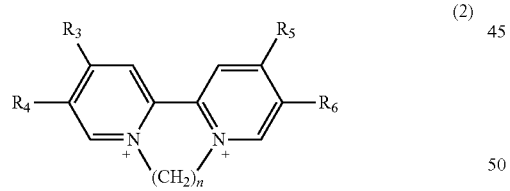
(2)

wherein n is an integer of 1 to 10, wherein R3 is a alkyl group substituted by a substituted or unsubstituted amino group, a aryl group substituted by a substituted or unsubstituted amino group, or a arylalkyl group substituted by a substituted or unsubstituted amino group, and the alkyl group has 1 to 12 carbon atoms, the aryl group has 6 to 20 carbon atoms, and the arylalkyl group has 7 to 20 carbon atoms, wherein R4, R5, and R6 are each independently a substituted or unsubstituted alkyl group, a substituted or unsubstituted aryl group, or a substituted or unsubstituted arylalkyl group, the alkyl group has 1 to 12 carbon atoms, the aryl group has 6 to 20 carbon atoms, and the arylalkyl group has 7 to 20 carbon atoms;

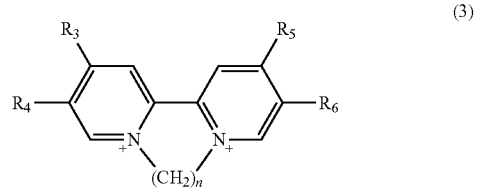
(3)

wherein n is an integer of 1 to 10, wherein R4 is a alkyl group substituted by a substituted or unsubstituted amino group, a aryl group substituted by a substituted or unsubstituted amino group, or a arylalkyl group substituted by a substituted or unsubstituted amino group, and the alkyl group has 1 to 12 carbon atoms, the aryl group has 6 to 20 carbon atoms, and the arylalkyl group has 7 to 20 carbon atoms, wherein R3, R5, and R6 are each independently a substituted or unsubstituted alkyl group, a substituted or unsubstituted aryl group, or a substituted or unsubstituted arylalkyl group, the alkyl group has 1 to 12 carbon atoms, the aryl group has 6 to 20 carbon atoms, and the arylalkyl group has 7 to 20 carbon atoms;

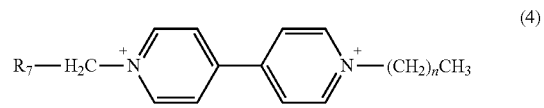
(4)

wherein n is an integer of 0 to 10, R7 is a substituted or unsubstituted amino group;

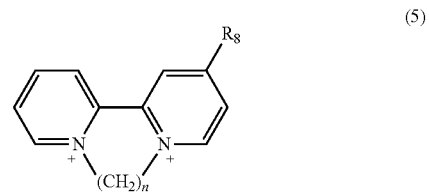
(5)

wherein n is an integer of 1 to 10, R8 is a substituted or unsubstituted amino group;

contacting a substrate, the reduced artificial electron carrier, and NAD-dependent dehydrogenase to produce a reduced substrate.

2. The method of claim 1, wherein the NAD-dependent dehydrogenase is selected from the group consisting of formate dehydrogenase, aldehyde dehydrogenase, alcohol dehydrogenase, lactate dehydrogenase, and glutamate dehydrogenase.

3. The method of claim 1, wherein the artificial electron carrier is the compound of the formula (8) or (9):

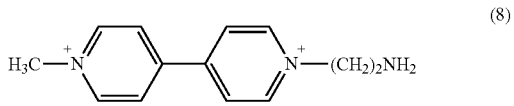
(8)

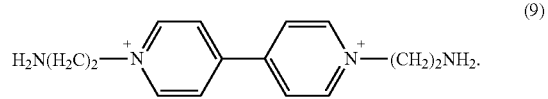
(9)

4. The method of claim 1, wherein the reducing agent is selected from the group consisting of sodium dithionate, sodium dithionite, ascorbic acid, and hydrazine.

5. A method of converting carbon dioxide into formic acid, comprising:

contacting an artificial electron carrier with an electron donor and photosensitizer and applying light to form a reduced artificial electron carrier, or contacting an artificial electron carrier with a reducing agent to form a reduced artificial electron carrier, wherein the artificial electron carrier is the compound of any one of the formulae (1) to (5):

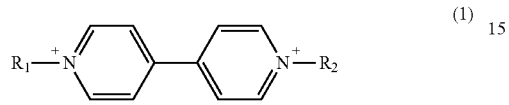

(1)

wherein R1 is a alkyl group substituted by a substituted or unsubstituted amino group, a aryl group substituted by a substituted or unsubstituted amino group, or a arylalkyl group substituted by a substituted or unsubstituted amino group, and the alkyl group has 1 to 12 carbon atoms, the aryl group has 6 to 20 carbon atoms, and the arylalkyl group has 7 to 20 carbon atoms, wherein R2 is a substituted or unsubstituted alkyl group, a substituted or unsubstituted aryl group, or a substituted or unsubstituted arylalkyl group, and the alkyl group has 1 to 12 carbon atoms, the aryl group has 6 to 20 carbon atoms, and the arylalkyl group has 7 to 20 carbon atoms,

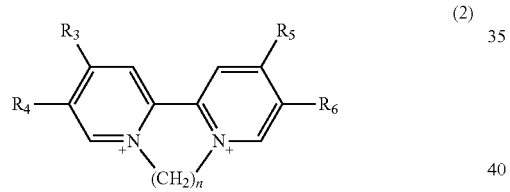

(2)

wherein n is an integer of 1 to 10, wherein R3 is a alkyl group substituted by a substituted or unsubstituted amino group, a aryl group substituted by a substituted or unsubstituted amino group, or a arylalkyl group substituted by a substituted or unsubstituted amino group, and the alkyl group has 1 to 12 carbon atoms, the aryl group has 6 to 20 carbon atoms, and the arylalkyl group has 7 to 20 carbon atoms, wherein R4, R5, and R6 are each independently a substituted or unsubstituted alkyl group, a substituted or unsubstituted aryl group, or a substituted or unsubstituted arylalkyl group, the alkyl group has 1 to 12 carbon atoms, the aryl group has 6 to 20 carbon atoms, and the arylalkyl group has 7 to 20 carbon atoms;

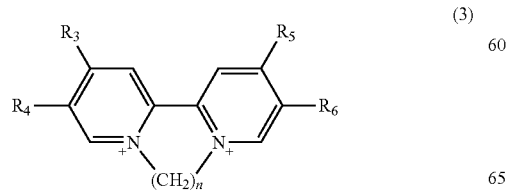

(3)

wherein n is an integer of 1 to 10, wherein R4 is a alkyl group substituted by a substituted or unsubstituted amino group, a aryl group substituted by a substituted or unsubstituted amino group, or a arylalkyl group substituted by a substituted or unsubstituted amino group, and the alkyl group has 1 to 12 carbon atoms, the aryl group has 6 to 20 carbon atoms, and the arylalkyl group has 7 to 20 carbon atoms, wherein R3, R5, and R6 are each independently a substituted or unsubstituted alkyl group, a substituted or unsubstituted aryl group, or a substituted or unsubstituted arylalkyl group, the alkyl group has 1 to 12 carbon atoms, the aryl group has 6 to 20 carbon atoms, and the arylalkyl group has 7 to 20 carbon atoms;

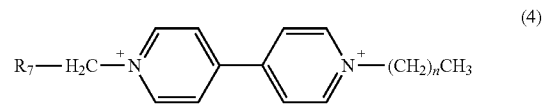

(4)

wherein n is an integer of 0 to 10, R7 is a substituted or unsubstituted amino group;

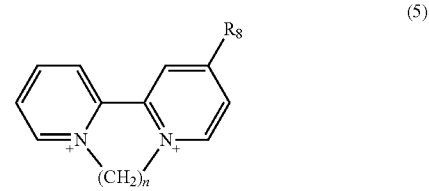

(5)

wherein n is an integer of 1 to 10, R8 is a substituted or unsubstituted amino group;

contacting carbon dioxide, the reduced artificial electron carrier, and formate dehydrogenase to produce formic acid.

6. The method of claim 5, wherein the artificial electron carrier is the compound of the formula (8) or (9):

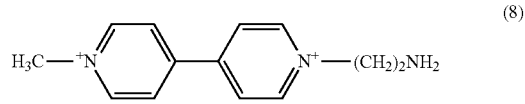

(8)

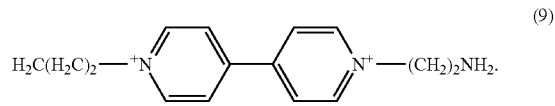

(9)

7. The method of claim 5, wherein the reducing agent is selected from the group consisting of sodium dithionate, sodium dithionite, ascorbic acid, and hydrazine.

8. A method of claim 5, further comprising the methanol producing steps (i) and (ii):

(i) converting the formic acid into a formaldehyde by an aldehyde dehydrogenase with a viologen compound or a bipyridinium salt derivative as an electron carrier;

(ii) converting the formaldehyde into a methanol by an alcohol dehydrogenase with a viologen compound or a bipyridinium salt derivative as an electron carrier.

9. The method of claim 8, wherein the electron carrier in the step (i) and the electron carrier in the step (ii) is the compound of formula (8) or formula (9).

* * * * *